United States Patent [19]

Liffmann et al.

[11] Patent Number: 5,037,737
[45] Date of Patent: Aug. 6, 1991

[54] ANALYSIS BY SENSOR PLACEMENT IN RECPROCATING FLOW

[75] Inventors: Stanley M. Liffmann, Andover; Humayun Qureshi, Wayland; John D. Czaban, Beverly, all of Mass.

[73] Assignee: Apec, Inc., Danvers, Mass.

[21] Appl. No.: 213,258

[22] Filed: Jun. 29, 1988

[51] Int. Cl.$^5$ .......................... C12Q 1/54; C12Q 1/60; C12Q 1/06
[52] U.S. Cl. ........................................ 435/11; 435/14; 435/39; 435/288; 435/291; 435/817; 436/34; 436/52; 204/403; 204/153.1; 204/153.12
[58] Field of Search ...................... 435/291, 11, 14, 39, 435/288, 817; 436/34, 52; 204/403, 1 T

[56] References Cited

U.S. PATENT DOCUMENTS

| | | |
|---|---|---|
| 3,539,455 | 11/1970 | Clark . |
| 3,700,335 | 10/1972 | Seelbinder ........................ 356/201 |
| 4,073,713 | 2/1978 | Newman . |
| 4,153,513 | 5/1979 | Edelmann et al. ............ 195/103.5 R |
| 4,311,789 | 1/1982 | Nylen et al. ...................... 435/10 |
| 4,490,235 | 12/1984 | Calzi . |
| 4,636,473 | 1/1987 | Keinstreuer ...................... 435/289 |
| 4,759,828 | 7/1988 | Young et al. ...................... 204/1 |
| 4,859,422 | 8/1989 | Qureshi et al. ...................... 422/81 |

FOREIGN PATENT DOCUMENTS 0304947 1/1989 European Pat. Off. .

OTHER PUBLICATIONS

Biotechnology Advances, vol. 3, No. 2, 1985, pp. 209-218, Pergamon Press Ltd., Oxford, GB; A. Graham et al.: "Biosensors: regent trends".
Biochimica et Biophysica Acta, vol. 384, 1975, pp. 307-316, Elsevier Scientific Publishing To., Amsterdam, NL; J. Campbell et al.: "The preparation of several new nylon tube-glucose oxidase derivatives and their incorporation into the reagentless automated analysis of glucose".

Primary Examiner—David L. Lacey
Assistant Examiner—J. D. Waack
Attorney, Agent, or Firm—Wolf, Greenfield & Sacks

[57] ABSTRACT

A method and apparatus for analyzing a sample to determine an analyte content has a sensor for sensing the analyte positioned between a first and second transducer. The analyte or derivatives thereof are reciprocated between the first and second transducer to reciprocate at the sensor and allow instantaneous sensing of an indication of the analyte's presence at a point between the first and second transducer. Rapid analysis can be carried out in many different systems including for example where the transducers are enzyme reactors and the analytes are body metabolites.

14 Claims, 4 Drawing Sheets

ANALYSIS BY SENSOR PLACEMENT IN RECPROCATING FLOW

BACKGROUND OF THE INVENTION

A large number of analyzing means and methods for various analytes are known in the medical and other processing arts. In many cases, immobilized enzyme membranes and enzyme reactors are coupled with electrochemical or other detectors to obtain indications of analyte concentration in various media such as body fluids and the like. T he chemistry for analyzing y means of $O_2$ sensors, pH sensors and the like, of materials such as glucose, creatinine and gases in blood such as $CO_2$ are known.

British Patent 1,485,123 published Sept. 8, 1977 to National Research Development Corporation discloses the utility of enzymes and other biologically active material in biochemical reactions which can be attached to solid supports and used to determine the analyte contents of body fluids. A tubular reactor having a solid support and carrying an enzyme is specifically described for use in a blood glucose determination as well as other determinations.

In such known methods, a nylon tube having a solid support on which is mounted glucose oxidase is used as a reactor. A sample of body fluid or diluted body fluid, for example, passed through the tube and reacted with the glucose oxidase and the oxygen consumed is monitored with a standard oxygen sensor such as described in U.S. Pat. No. 3,539,455 of Leland C. Clark. Such enzyme reactions have long been known for use. In some cases, reactions carried out in this manner are limited in speed and do not maximize the efficiency possible with automated equipment.

SUMMARY OF THE INVENTION

It is an object of this invention to provide a means and method for analyzing a sample to determine an analyte content thereof rapidly and efficiently.

It is still another object of this invention to provide a means and method in accordance with the preceding object wherein a fluid is passed back and forth between two transducers with an intermediate sensor for sensing and determining analyte content of an unknown sample rapidly with good accuracy.

Still another object of this invention is to provide an enzyme reactor useful in carrying out the methods of the present invention.

Still another object of this invention is to provide means particularly adopted for us in connection with analytical determinations of an analyte in a rapid and efficient manner.

According to the invention, a method of analyzing a sample to determine an analyte content thereof is carried out by passing the sample or a derivative thereof to a first transducer and a second transducer and reciprocating between said first and second transducer while sensing an indicator of said analyte's presence at a point between said first and second transducer.

Preferably the apparatus for carrying out the method in the case of an immobilized enzyme based test comprises a first modular tubular reactor and second modular tubular reactor which are mounted in a block or housing and removable therefrom. A conduit between the reactors extends to a sample chamber interconnected with an electrode sensor such as an $O_2$ sensor.

In the preferred embodiment, the method is carried out for use in testing biological fluids for metabolites, and an electrochemical sensor in the form of an electrode is positioned between two reactors used. A determination of the concentration of metabolite is preferably obtained in short time periods of for example 60 seconds or less. Preferably, the space within which fluid is exposed to the sensor for test is dimensioned to be such that the reactor chamber areas are at least two times said space and more preferably at least four times the test space to allow rapid reciprocation of liquids between the two reactors and rapid readout of results.

It is a feature of the method and apparatus used that the testing can be carried out rapidly and efficiently at high fluid throughputs. Long life reactors can be used which can be interchanged in various systems. Maintenance can be minimized and small sample size can be used. Since automated equipment can easily be designed, unskilled operation is possible. The method and apparatus can be used with various transducers including immobilized enzyme reactors and dialysis arrangements.

BRIEF DESCRIPTION OF THE DRAWINGS

The above and other objects, features and advantages of the present invention will be better understood from the accompanying drawings in which.

PREFERRED EMBODIMENTS OF THE INVENTION

Figure 1:
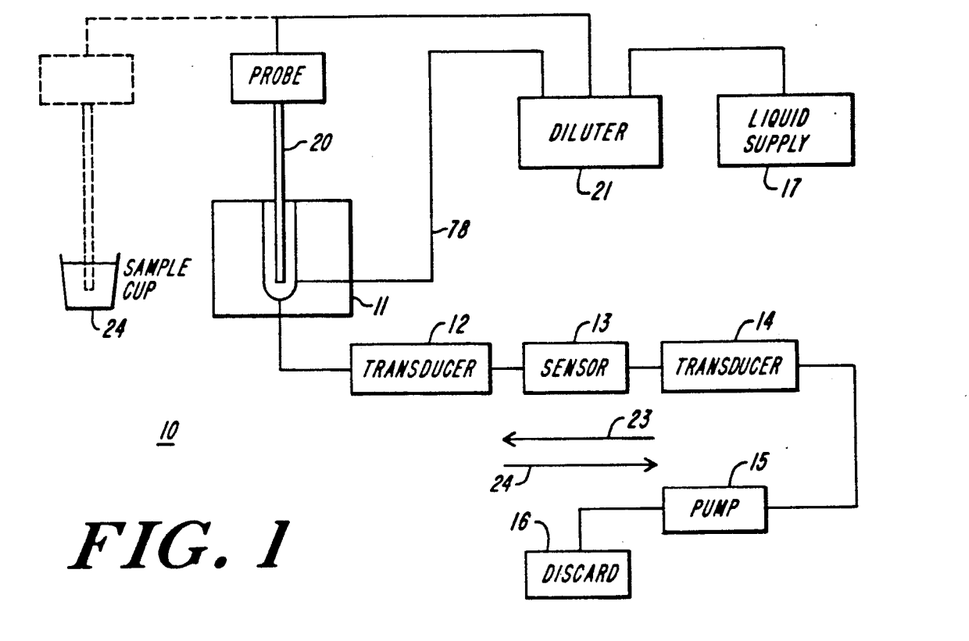
FIG. 1 is a block diagrammatic view of an embodiment of a system in accordance with the present invention.

A testing apparatus and method in accordance with the present invention is diagrammatically shown at FIG. 1 in a system for testing a sample material. Basically, the method and apparatus of this invention can allow the carrying out of clinical diagnostic testing and analytical measurements of dissolved organic and inorganic molecules and liquids using optical, gas, ion or other sensors. The key feature of the invention is the use of a sensor mounted between two transducers for reciprocation of a test fluid therebetween whereas the prior art has often mounted the sensor before or after a sensing surface or transducer.

The means and method of the present invention can be used in clinical or process testing of various metabolites such as BUN, glucose, creatinine, uric acid, total bilirubin, total cholesterol, triglycerides and the like; blood gases such as oxygen, carbon dioxide; enzymes such as CPK amylase, SGPT, LDH, SGOT, alkaline phosphatase; therapeutic drugs such as theophyline; hormones such as thyroxin, T4; proteins such as albumin, alpha feto, IgG, IgA, IgE and other materials wherever rapid testing is desired in the range of preferably less than five minutes and more preferably in less than one minute. For example, glucose testing can be carried out in less then 45 seconds.

The sensors used in the present invention can be any conventional electrochemical or other sensor arrangements as known in the art. Such sensors include standard $CO_2$ electrodes, pH electrodes, optical curvettes positioned between two transducers where photo multiplier tubes and interference filters can be used to obtain optical readouts with the use of fiber optic light sources or the like or gas dialysis blocks for sensing gases generated from the analytes indicated above.

As used in this specification and claims, the analytes can be any of the materials to be tested utilizing the system and apparatus of this invention and include the material generated from such analytes in the testing process. For example, $O_2$ is actually sensed in the preferred process of testing to determine glucose content of a sample. Similarly, $O_2$ is tested at a $O_2$ electrode when testing for cholesterol using immobilized enzymes reactors. Similarly, blood gas determinations require the use of gas permeable membranes in dialysis blocks but should be considered within the scope of the analyte meaning as used in this application.

Any sensor can be used including optical amperometeric, conductimeteric, thermal or potentiometric type sensors. In some cases, multiple sensors can be positioned between the transducers.

The transducer used on either side of the sensor in the present invention can be of various structures. In the preferred embodiment, immobilized enzyme reactors are used. Such reactors can comprise tubular members having solid supports for enzymes which react with sample material during flow through the tubular members. The transducers can be reactors of other types which allow flow therethrough or can be gas dialysis blocks. Heaters, irradiators, catalyst chambers or the like can be the transducers used.

In each case, the dead volume or space where sensing occurs is small with relation to the transducer or reactor on either side of the sensor. Preferably, the reactor space of each reactor on either side of the sensor is at least four times, preferably eight or more times the dead space in which sensing occurs. While the two reactors are preferably identical, they can be different in size, content or other value.

In all cases, a reciprocal motion of a fluid between the sensor and transducers surrounding it is used with sensing carried out preferably during the reciprocal motion of the fluid to determination rate of reaction. In some cases, end point or steady state is useful to obtain rapid readout of results to determine concentration of the analyte being tested for in the process. In the preferred embodiments bulk conversion of analytes in mobilized enzyme reactors is carried out with simultaneous sensing of the reaction as it progresses.

It is best shown in FIG. 1, the system 10 provides for fluid passageways or conduits between a mixing chamber 11, first transducer 12, sensor 13, second transducer 14, peristaltic pump 15 and discard area 16. Fluid supply means are shown at 17 interlinked with the mixing chamber through diluter 21. A probe 20 is connected to the fluid diluter 21 and is capable of moving to a sample chamber area 22 as shown in the dotted position to pick up a sample, which can be diluted prior to the probe being positioned within the mixing chamber 11 to discharge the diluted sample. Alternately, as preferred the sample is diluted with the fluid supply 17 directly through line 78 to the mixing chamber 11.

The diluter 21 can be a conventional syringe-type diluter or more preferably is a multi-mode differential dilution pump arrangement as described in applicants' copending application filed simultaneously herewith entitled: Multi-Mode Differential Fluid Displacement Pump the entire specification and drawings of which are incorporated by reference herein. Such a dilution system comprises a defined volume chamber having at least two different diameter pistons mounted for movement therein whereupon fluid displaced by one or both of said pistons comprises a first volume and fluid dispensed by the second of said pistons comprises a second volume enabling dilution of a sample as described therein.

The sample fluids are preferably liquids and may comprise blood, serum, plasma, spinal fluid, urine, cell culture media, industrial liquids containing analytes or other samples to be tested. The liquid supply 17 and diluter 21 can provide for cleaning or flushing materials to be entered into the mixing chamber and system or alternately, for reactants or carriers such as buffer systems or inert carrier liquids when testing samples of various types.

The peristaltic pump 15 can be of conventional design and is designed to move the liquid within the system reciprocally in the directions of arrows 23, 24 during testing or sensing.

Figure 2:
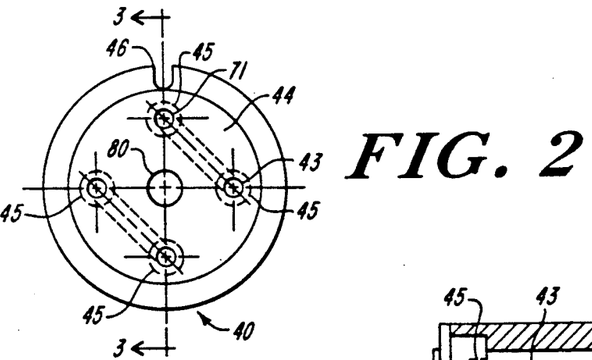
FIG. 2 is a top plan view of an enzyme reactor useful therein.
Figure 3:
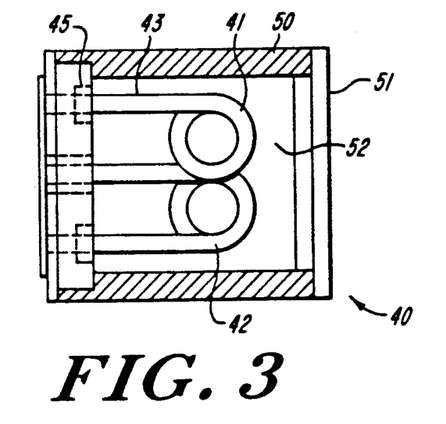
FIG. 3 is a cross-sectional view thereof through line 3—3.

In the preferred embodiment of this invention, transducers 12 and 14 are enzyme reactors having enzyme attached to solid supports to form a biologically active matrix within a tubular reactor as best shown in FIGS. 2 and 3. Tubular reactors per se are known as is their use in testing for glucose or other analytes. Glucose determination in immobilized enzyme reactors are described in British Patent 1,485,123, Published Sept. 8, 1977. In such reactors, there is usually a hollow tube of an organic polymer suitable for use as a support for biologically active material. The tube can comprise a water insoluble polymer having a wall carrying primary or secondary amido groups, amino substituted aromatic groups or nitrile groups to convert at least some of the amido, amino or nitrile groups on the inner surface of the tube to imidate groups capable of linkage reaction with a biologically active material. Such conversion is affected without substantial cleavage of the polymer backbone.

The organic polymer which may comprise primary or secondary amido groups, amino-substituted aromatic groups, or nitrile groups may be a synthetic polymer such as for example polyacrylamide or homologues thereof (primary amido groups), a nylon, a polyurethane or a urea-formaldehyde polymer (secondary amido groups), polyaminostyrene (amino groups), or polyacrylonitrile (nitrile groups). Excellent results are obtained using nylon and this is the preferred polymer.

The organic polymer is preferably in the shape of a hollow circular tube although other shapes can be used. Primary or secondary amido groups may be converted to imidate groups using an alkylation reagent, for example a dialkyl sulfate such as dimethyl sulphate or diethyl sulphate, ethyl chloroformate, an alkyl halide such as iodomethane or iodoethane, or a triethyloxonium salt. The reaction is preferably carried out at room temperature but can be at temperatures for example from 30° to 100° C. The alkylation reagent may be dissolved in a suitable organic solvent, for example methylene chloride or toluene, if necessary. Amino groups substituted in aromatic nuclei may be converted to imidate groups by reaction with ortho esters. Nitrile groups may be converted to imidate groups by condensation with an alcohol in the presence of an acid.

A wide range of biologically active materials may be linked to the organic polymers to produce biologically active matrices. These include enzymes present in or isolated from animal, plant or micro-biological tissue such as, for example, proteolytic enzymes such as trypsin, chrymotrypsin and pepsin; hydrolases such as galactosidase, ribonuclease, alkaline phosphate, amyloglucosidase, dextranase; cholesterol esterase, urease, penicillinase and invertase; dehydrogenases such as lactic dehydrogenase, liver alcohol dehydrogenase, yeast alcohol dehydrogenase and glucose-6-phosphate dehydrogenase; kinases such as creatinine phosphokinase, pyruvate kinase and hexokinase; oxidases such as glucose oxidase, cholesterol oxidase and catalase; transaminases such as glutamate-pyruvate transaminase and glutamate-oxalacetate transaminase; and amidases such as amidase and penicillin amidase. Alternatively, the biologically active material may be a co-factor such as, for example, nicotinamide adenine dinucleotide (AND), nicotinamide adenine dinucleotide phosphate (NADP) and their reduced forms, adenosine diphosphate ribose (ADP-Ribose), adenosine triphosphate (ATP), adenosine diphosphate (ADP), adenosine monophosphate (AMP), pyridoxamine phosphate, pyridoxal phosphate, a pterin, a flavin, or co-enzyme A; an inhibitor such as, for example, an organophosphorus compound; or an antigen or antibody. The linking reaction in which the biologically active material is covalently bound to the organic polymer is preferably carried out under very mild conditions. Alkaline conditions are preferred, and the most favourable pH at which to bind the biologically active material to the organic polymer is the highest pH which the biologically active material in solution can tolerate without losing its activity. Usually this pH is within the range of from 7 to 10, and preferably from 7.5 to 9.

A further description of nylon tube glucose oxidase derivatives and their use in the automated analysis of glucose is further described in Biochimica Et Biophysica Acta, 384 (1975), page 307–316, Campbell, Hornby and Morris, *The Preparation of Several New Nylon Tube Glucose Oxidazed Derivatives and Their Incorporation Into the Reagentless Automated Analysis of Glucose.*

With reference now to FIGS. 2 and 3, an enzyme reactor is shown which is suitable for use as a removable or disposable module in a system of the type shown in FIG. 1. In this case, a enzyme module 40 can replace the transducers 12 and 14 in that two reactors are contained within the module 40. The first reactor 42 is substantially identical to reactor 43 and only one will be fully described. The reactors comprise tubular members of nylon having a wall thickness of 0.015 inch and each having a length of 7.0 inch. The tubes are coiled intermediate their ends as best shown in FIGS. 2 and 3. The ends of the tube 41 of each reactor is mounted in a header 44 at circular recesses 45 and potted therein by an epoxy sealant not shown. The header 44 has through holes for the ends of the tubular reactors which can interengage with O-ring liquid seals (not shown) of a mixing chamber block or housing 11, and carries an outer notch 46. Notch 46 and bore 80 act together as a locating notch and bore when the module is plugged into an operating block of a testing device in accordance with the present invention.

Preferably the inside diameter of the tubes can be from 0.020 to 0.088 inch and the tubes can have lengths from 1.5 inches to 12 inches or more when uncoiled. The reactors are encased within a cylindrical shell 50 of hard plastic with an end closure plate 51 sealed at an edge as known in the art. The internal volume 52 can be filled with a heat dissipating material such as a filled epoxy resin as known in the art.

Figure 6:
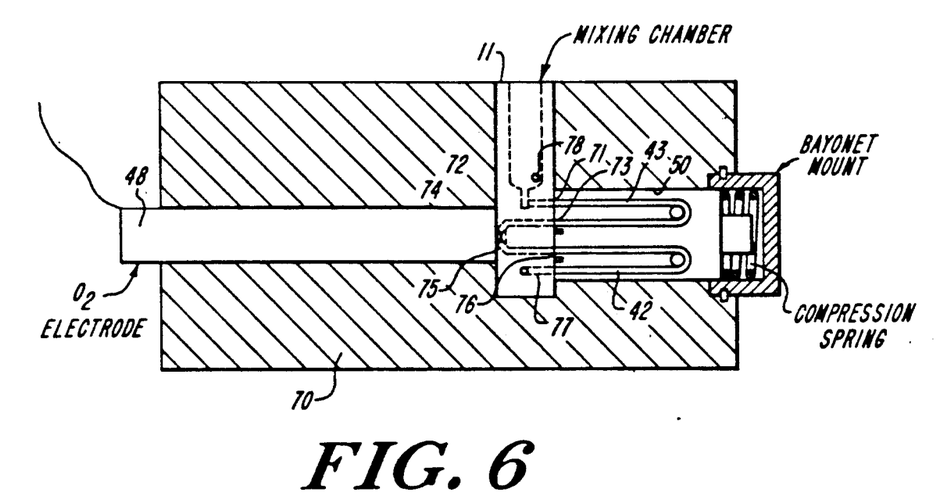
FIG. 6 is a view through a preferred embodiment of a mixing chamber block carrying an electrode assembly and reactor assembly in accordance with the present invention.

Reactors of this type can be used as replaceable modules in automated equipment as when used in a reactor and mixing block of the type diagrammatically shown in FIG. 6.

Figure 4:
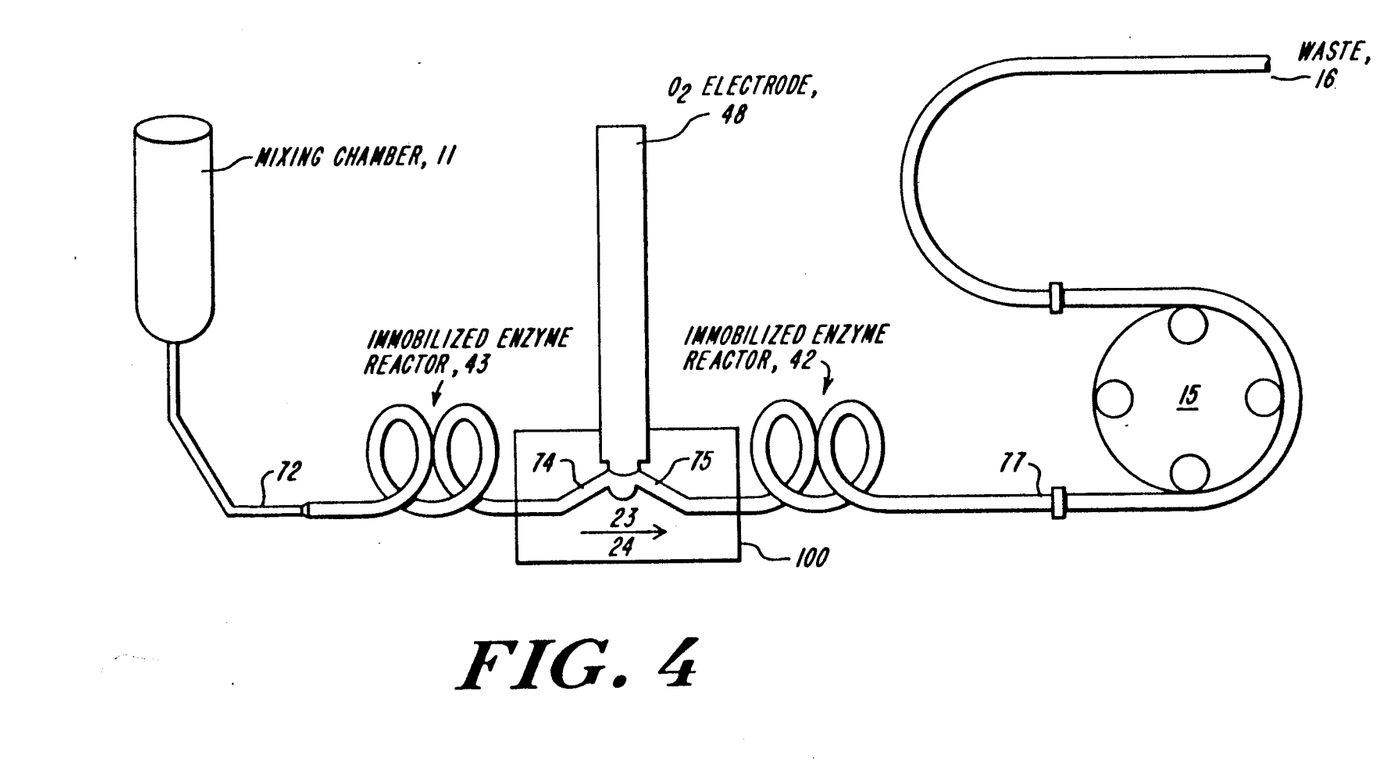
FIG. 4 is a semi-diagrammatic view of a preferred immobilized enzyme reactor system in accordance with this invention.

An operating block 70 for the system 10 is diagrammatically shown at FIG. 6. Note that FIG. 4 shows a mixing chamber 11, first reactor 42, second reactor 43, $O_2$ electrode 48 with a peristaltic pump 15 and a waste area 16. The peristaltic pump is capable of moving the fluid in the direction of arrows 23, 24 as desired.

In the embodiment of FIGS. 4 and 6, the reactor shell 50 fits within a tubular bore 60 in a aluminum block 70 of an automated test apparatus. A spring loaded cap 61 retains the reactor in the block with the O-ring seals pressed against corresponding passageways within the block.

The chamber 11 can be an insert block of plexiglass. In a typical setup, one end of a reactor tube as at 71 can be connected to an outlet 72 from the mixing chamber 11, outlet 73 can lead to a passageway 74 of an $O_2$ sensor 48. Reactor 42 has one end O-ring sealed tube and interconnected with a passageway 75 of the electrode 48 as at 76 and a second end as at 77 interconnected with a fluid passageway to the peristaltic pump 15. Preferably, the mixing chamber is in a slide-in block having the fluid passageways noted between the reactor shell 50 and the electrode 48 as diagrammatically illustrated in FIG. 6.

Figure 5:
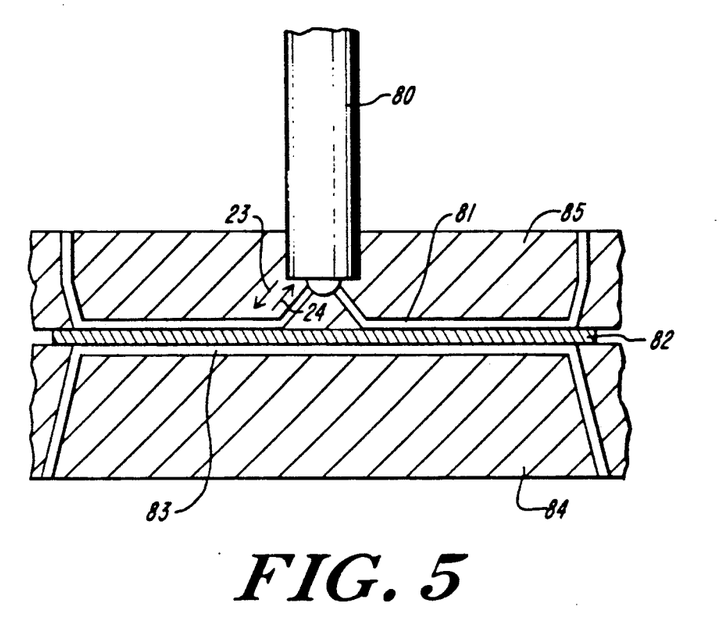
FIG. 5 is a semi-diagrammatic, cross-sectional view through a transducer arrangement in which a gas dialysis block is used to detect gas passing through a gas permeable membrane extending on either side of a sensor.

In another embodiment of the invention where gases are sensed, the transducers can be in the form of gas dialysis blocks as diagrammatically shown in FIG. 5. In transducers of this type, a pH sensor 80 of known design can be used having a face adjacent a first conduit or passageway 81 which can carry a flow of buffer on one side of a gas permeable membrane 82 with a flow of sample or diluted sample passing through passageway 83 on another side of the gas permeable membrane. Conventional gas dialysis blocks 84, 85 can be used, however, the electrode 80 is mounted in the center of the gas dialyzer with a minimum of dead space volume between the active dialyzer surface and the electrode surface. In this case, gas from the sample flowing in passageway 83 passes through the membrane which has a portion on either side of the sensor and thus lies on either side thereof. Reciprocal movement of the buffer or any other fluid for capturing the gas in conduit 81 is shown at arrows 23, 24. This enables a sensing of the gas through pH detection of the pH electrode 80 or other sensors as known in the art. The $CO_2$ gas generated changes the pH of the buffer.

In the case of glucose determinations as well as cholesterol determinations, the rate of of decrease of $O_2$ is measured as an electrode current as the reaction progresses and the liquid reciprocates between the reactors. This rate in the case of glucose and the steady state current in the case of cholesterol is an indication of glucose, or cholesterol concentration respectively. The rate or steady state current is read as an electrical readout through the electrode.

The electrode used is preferably in a module form similar to the module form of the reactors. This allows plugging into the block 70 previously described. Thus, an electrode in the form of sensor 13 can be a tubular electrode having a membrane face which membrane is directly exposed to the fluid flow in the fluid passageway between the immobilized enzyme reactors 42 and 43 as best seen in FIG. 4.

In FIG. 4, the sample dead space area is within passageways 74, 75 and facing the $O_2$ electrode. The area is bound by the ends of the reactors 42, 43 contacting 74 and 75. A diluted sample is pulled into the sensor area with the peristaltic pump and passed by the sensor at least 4 times the dead volume of the sensor area in the tubes 74, 75. The pump can them be halted and rotated forward the number of steps required to move a volume of liquid eguivalent to approximately 5 times the dead volume of the sensor space. This sensor space is preferably in the form of a bore through a cuvette or block 70. In FIG. 4 the cuvette is diagrammatically indicated at 100. The pump direction can be reversed and the head rotated the same number of steps in the backward direction. The forward and backward rotation can continue for a specified number of cycles for each species to be analyzed. The data can be taken during the cycling, the sample then flushed with diluent or cleaning fluid and the cycle stopped with diluent left in the sensor area. Thus, the process is ready for immediate repeat.

In the preferred embodiment for measuring glucose, immobilized glucose oxidase is used on nylon tubing having an inside diameter of 0.86 millimeters. The sensor is an $O_2$ electrode having a membrane of 0.75 mil polyethylene. The serum sample is human serum diluted 1:65, pulled into the reactor electrode dead space area with a conventional peristaltic pump. The pump is then rotated a given number of steps forward and the same number of steps in a reverse direction. The number of steps correspond to a particular volume of fluid which in the preferred embodiment is 4 times the dead space volume in the electrode cuvette providing the passageways 74, 75. For example, when the dead space volume and the cuvette is 10 microliters, the rocking volume should be approximately 40 microliters. The reactor volume in each reactor should be approximately 2 times the rocking volume (one back and forth movement). The number of rocking cycles for glucose can be 7 with the start of data being taken at the end of the second cycle. Data is then taken for five cycles. The rate of decrease in $O_2$ concentration is then computed and compared to the rate of the standard. From this, a value for the unknown concentration of glucose in the sample can be computed. Preferably, the temperature is maintained at 33° C. and the total cycle time is less than 50 seconds. Ten microliters of sample can be used in an extremely short time to give desirable results.

The dead space around the sensor 48 starts at the interface to each of the reactors on either side of the sensor and comprises the fluid conduit through which liquid flow passes from the first to second reactor or transducer. In most cases, the reactors are fully lined with enzyme and reaction occurs at the very start. In the preferred embodiment, the dead space maintained is small in the order of from 2 to 20 microliters but could be 100 microliters or more. The volume in each reactor is at least four times the dead volume but preferably at least eight times or more as for example in the preferred embodiment each reactor has a space for fluid in its tubular conduit of 90 microliters. With normal peristaltic pump action, reciprocation of the fluid over the sensor can be carried out rapidly and results can be obtained in time periods of less than one minute and preferably 45 seconds. The specific reactors used can have long lives although they are replaceable as modules as shown in FIGS. 2 and 3. Preferably, they have life spans of at least two months which in normal usage would permit testing of at least 10,000 samples. Reaction temperatures within the reactors are preferably maintained at 32° C. while suitable temperature control means not shown. The reactors are preferably surrounded by material having high thermal•conductivity to allow temperature regulation of the reactors. While spring-clip or bayonet-type mounting as shown in FIGS. 2 and 3 is preferred, various constructions for a replaceable module can be used.

The mixing chamber is preferably in the form of a clear see through plastic block in module form as shown in FIG. 6. The block automatically interconnects its side passage 78 with a fluid supply for cleaning and diluting if required and a bottom passage 72 with one of the two reactors used. The mixing chamber module is positioned adjacent the reactors in the mounting block as well as in proximity to the $O_2$ probe when glucose is to be determined. The chamber 11 is in effect a fluid module. Preferably it has a ½ sphere bottom. The reagent is introduced from the line 78 through a hole offset from the center of the axially elongated chamber 11 and at least ½ of the distance from the start of the spherical bottom to the bottom end of the chamber. This creates a swirling vortex within the well which is useful for cleaning, mixing and maintaining uniformity of the sample to be tested. The sample to be tested can be diluted prior to entrance to the chamber 11.

In the preferred embodiment, where glucose is to be tested, the probe moves from the sample cup 24 to the chamber or well 11 after picking up the sample and positions the diluted or full sample as the case may be in the chamber 11. Buffer which can be introduced through line 78 cleans the outside of the probe. A peristaltic pump can be used to evacuate the chamber and part of the reactors leaving liquid around the electrode or perhaps evacuates the entire fluid system. Diluent can be introduced from line 78 in an amount of for example 150 microliters into the chamber 11. With the probe 20 tip below the liquid level in chamber 11, the sample which can be 10 microliters, is dispensed within the chamber 11 and then the probe is withdrawn from the chamber. An additional quantity of buffer as for example 450 microliters can be introduced to chamber 11 through line 78 in the form of a swirling vortex at a speed of 20 milliliters per minute into the sample chamber to form a volume of 650 ml. About 650 microliters of total liquid is preferably used in the test of this invention. The mixture from the chamber 11 is then drained into the reactors 42 and 43 as well as the dead space within the $O_2$ sensor. Additional buffer from supply 17, as for example 700 microliters, cleans the walls and the outside of the probe. Everything within the chamber 11 can then be drained to a waste area. The chamber 11 is then filled with air. 300 microliters of buffer can then be entered through line 78 into the chamber 11 and to fill the reactors and electrode after the test. It should be noted that the reactors have a coiled section in order to compact the size of the reactors.

Because the probe can be introduced into the chamber with fluid flow as described, the chamber 11 can be used for both cleaning the probe and mixing or holding the sample for delivery to the reactors. Because the entrance port 78 is offset from the central axis of the elongated chamber and is positioned part way up the spherical curve of the bottom, force of the diluent or other fluid through line 78 creates a swirling vortex for mixing and cleaning. Draining at the bottom of the spherical bottom allows complete draining from the chamber 11. Minimized cleaning fluids can be used and small modules can be used since the fluid use is maximized. The outlet 78 is preferably at least half a way to the bottom of the spherical curved bottom portion of the chamber 11. This portion is a half sphere. Access must be provided at the top of the chamber for the probe so that the chamber 11 in effect has an upper access port, a lower drain port and an intermediate fill port.

It should be understood that the use of dialysis membranes as the transducers can be in the form of two separate transducers just as there are two reactors in FIG. 4. Alternately, a single membrane arrangement of FIG. 5, effectively is a split transducer by locating the electrode 80 at the center point thereof.

Figure 7:
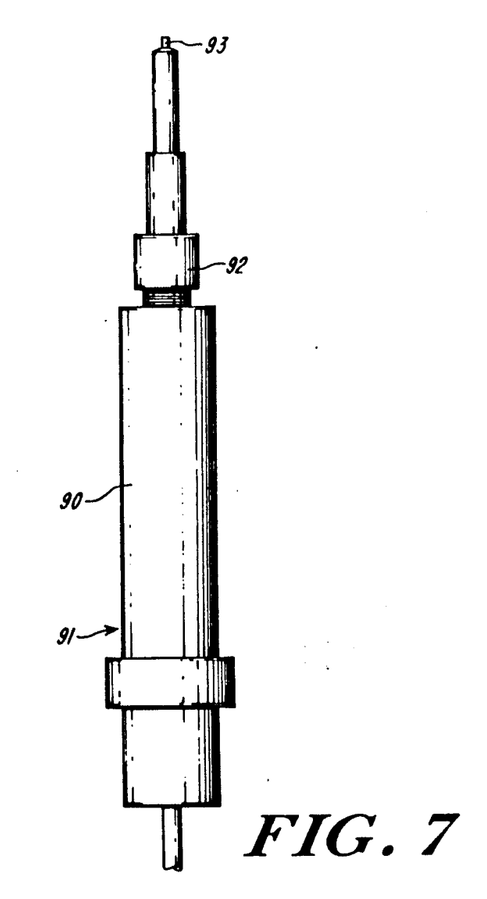
FIG. 7 is a plan view of the cartridge body of a sensor in accordance with this invention.
Figure 8:
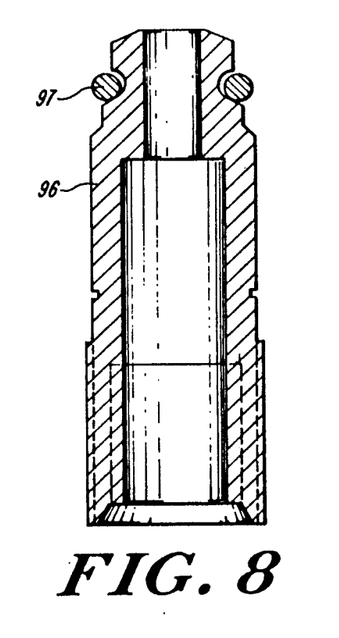
FIG. 8 is a cross-sectional view through the axial center line of a cartridge-type electrode sensor in accordance with this invention.

The sensors used in connection with this invention can vary as stated above. When an electrode sensor is used, it is preferred to use a cartridge type electrode sensor as known in the art. For example as shown in FIGS. 7 and 8, the sensor can have a cartridge body 90 of tubular cross section for fitting within the block 70 by a bayonet type arrangement as previously described (not shown). The electrode shown at 91 has a screw thread end 92 through which a platinum wire cathode 93 extends. The cathode 93 is covered by a membrane cap 94 screw threaded at 95. The cap 94 has a membrane 96 retained in place by an O-ring 97.

Cartridge-type replaceable membranes of this type can be made to fit within cuvette section 100 diagrammatically shown in FIG. 4. This replaceable cuvette forms a portion of the block 70. It carries the fluid passageways 74, 75 and an entrance bore for positioning the electrode 91 or 48, as for example shown in FIG. 4.

The membranes used with the $O_2$ electrodes of this invention can be any of several types. Clysar EH, a trademark product of Polymer Products Department of Dupont, Wilmington, Del. made of biaxially oriented polyethylene film having thicknesses of from 0.6 to 1.0 mil (nominal) can easily be used with a preferred thickness of 0.75 mil. Clysar EHC, a biaxially oriented polyethylene/polypropylene copolymer film also available from Dupont is useful. Other useful membranes for the electrodes of this invention include Cryovac MPD 2055, a trademark product of W. R. Grace & Co. of Duncan, S.C. comprising a polyolefin multi-layered film in thicknesses of from 0.5 to 1.0 mil and Cryovac D-955, a polyolefin cross-linked multi-layered film. TEFLON film sold under the tradename NEN-FLO having a thickness of from 0.5 to 1.0 mil and manufactured by Dupont is preferred for certain glucose uses.

The $O_2$ electrode is a conventional $O_2$ electrode having a conventional electrical readout through known systems as known in the art. The Beckman $O_2$ electrode manufactured by Beckman Instruments, Inc. of Brea, Calif. can be used. This electrode is about 1.5 inches long with a rhodium cathode 5 millimeters in diameter and a silver anode. The electrolyte maintaining electrical contact between the anode and cathode is a highly viscus gel containing potassium chloride. The electrolyte is held in position by a Teflon membrane 1 millimeter thick which is pressed tightly against the cathode. Because of this pressure, only a thin layer of electrolyte is trapped between the cathode and teflon membrane. The anode is held at 0.55 volts versus the cathode. Only the TEFLON membrane is in contact with the solution in the passageways 74 and 75 in the preferred embodiment of this invention.

In a first specific example of this invention, the glucose content of a human serum sample is determined using a system of the type illustrated diagrammatically in FIGS. 1, 4 and 6. The electrode used is substantially similar to Beckman $O_2$ electrode as previously described, however, it has a small platinum cathode with a potential between the electrodes of 650 millivolts. Each of the two reactors 42 and 43 have a volume of 80 microliters and each are formed of a nylon tube having an inside diameter of 0.86 millimeters with a length of 17.5 centimeters coiled as shown and coated with glucose oxidase by activating nylon with triethyloxonium tetrafluoroborate (10% in methylene chloride). This is carried out by flow through for 20 minutes at 3° C. A flush with methylene chloride is used. 10% hexane diamine spacer in methanol is added and rapidly flowed through for one minute. The tube is then allowed to sit in hexane diamine for one hour after which it is flushed with distilled water. Reactivation is carried out with 5% gluteraldehyde pH 8.5 in a buffer. Washing at a pH of 7.8 with phosphate buffer is then carried out. Enzyme glucose oxidase is added in 900 units per/ml solution in a pH 7.2 phosphate buffer. This solution is allowed to remain at 4° C. for six hours. Tris buffer is then used to flush the tube of excess unattached enzyme.

The $O_2$ sensor is a platinum cathode electrode with silver anode as shown in FIG. 7 with the potential between the electrodes of 650 millivolts which can cause reduction of $O_2$ in the sample after passing through the membrane. The membrane is a 0.75 mil thick polyethylene sold by Dupont, Wilmington, Del. under the tradename CLYSARE H.

The sample is human serum but can, of course, be plasma, urine, spinal fluid, cell growth media or the like. The serum is diluted 1:65 in Tris buffer pH 7.2 in the sample chamber 11. The peristaltic pump is used to deliver and pull through the reactor the serum dilution and to move the solution back and forth. 400 microliters is pulled into the system shown in FIG. 1 with a reciprocation of about 40 microliters in six complete back and forth cycles.

The electrode output is read after the second reciprocation at eight spaced intervals to have two readings on each reciprocation Each back and forth reciprocation takes 1.6 seconds for a total analysis time of 9.6 seconds.

Time and picoamp output are measured at specific intervals and then a linear regression analysis is carried out to determine the best straight line through the points to test for the presence of glucose, thus assigning a slope to the line. This procedure is carried out for a known concentration of glucose and from which a calibration curve is determined and the slope of the unknown sample is then compared to determine glucose concentration. The reaction is carried out at 33° C.

Table 1 shows the target value of four control sera samples tested in the system.

TABLE 1

| TARGET VALUE (mg/deciliter) | SAMPLE (control/serum) | X (unknown measured value) | C.V. Within Run (% coefficient of variation) | C.V. (Day to Day) |
|---|---|---|---|---|
| 76 | MONI I | 72.5 | 1.13% | 1.80% |
| 258 | MONI II | 260.1 | 1.14% | 1.46% |
| 68 | SER CHEM I | 65.5 | 1.52% | 2.26% |
| 257 | SER CHEM II | 256.3 | 0.92% | 1.30% |

Note that three percent is considered a good C.V (percent coefficient of variation) in test instruments of this type. The above test data clearly indicates that accuracy and repeatability is good in the system of the present invention.

The above example involves the use of known glucose testing chemistry where the reactions occur as described below:

$$H_2O + Glucose + O_2 \rightarrow Gluconolactone + H_2O_2$$

In a second example using the system of this invention to determine cholesterol in a blood serum sample of a human, the first example is repeated with the following changes. The reactors used are identical except that the enzyme immobilized in the reactor is cholesterol esterase and cholesterol oxidase formed in the same manner as previously described in the first example with 3 milligrams per/ml of each used. The Tris buffer is repeated but added to it is 0.4% of Triton X100 produced by Rhom and Hass. Sodium chlorate is added to the buffer at a value of 0.2 millimolar along with magnesium chloride and ethylene diamine tetra acidic acid (EDTA) in an amount of 5 and 2.5 millimolar respectively. The reaction temperature varies between 20° to 40° C. and is preferably maintained at about 39° C.

The reaction of cholesterol in the blood with the enzyme immobilized in the reactor produces $O_2$ and is detected by the sensor.

Here again readout is carried out during the reciprocation of the diluted sample as the reaction approaches steady state as previously described.

Extremely accurate results can be obtained
The chemistry of this reaction is as follows:

$$Cholesterol\ Ester + H_2O \rightarrow Cholesterol + Free\ Fatty\ Acid$$

$$Cholesterol + O_2 \rightarrow Cholesterol + H_2O_2$$

In a third example of this invention, a 20 microliter serum sample is aspirated out of the probe and dispensed into the well 11 containing 20 millimoles of $H_2SO_4$ (100 microliters). The sample is mixed by rapid addition of 400 microliters of 20 millimole $H_2SO_4$. The diluted sample is then pulled into the gas dialyzer shown in FIG. 5 where the buffer flow is substituted by 4.0 millimoles sodium bicarbonate at a pH of 8.9. The sulfuric acid in the diluent causes the release of $CO_2$ gas from the sample as illustrated below:

$$NaHCO_3 + H_2SO_4 \rightarrow H_2CO_3 + NaHSO_4$$

$$H_2CO_3 \rightarrow H_2O + CO_2(l)$$

$$CO_2(l) \rightarrow CO_2(g)$$

The $CO_2$ gas dissolves in the membrane which is 1 mil thick and then passes through to the bicarbonate buffer side and undergoes the following reactions:

$$CO_2(g) \rightarrow CO_2(l)$$

$$CO_2(l) + H_2O \rightarrow H_2CO_3$$

$$Na_2CO_3 + H_2CO_3 \rightarrow 2NaHCO_3$$

This causes a decrease in pH of the bicarbonate buffer due to the $CO_2$ going from one side of the membrane to the other. The peristaltic pump controlling the bicarbonate is then rotated back and forth to bring the acidified buffer to the electrode.

This results in the rate of $CO_2$ evolution being sensed by the pH electrode, which rate is proportional to the bicarbonate concentration in blood in the range of 5–45 millimoles per liter. The total cycle time is less than one minute and an accurate readout of $CO_2$ content is obtained.

After the readout the buffer and the diluted sample flow on either side of the dialyzer membrane is flushed with fresh solutions which speeds the return to base line of the electrode.

While specific embodiments of this invention have been shown and described, it should be understood that many variations are possible.

Generally, it is preferred to have the system as described which reacts very rapidly. It is almost an instantaneous reaction and thus, is faster than a normal membrane electrode method, because the enzyme surface and the electrode surface are exposed to diluted sample which is constantly mixed because of the reciprocal motion of the fluid. Having the enzyme layer on the electrode creates a barrier to stirring which can only be traversed by diffusion of molecules through the layer. Thus, the response of the sensor slows down in some cases in particular during the recovery stage. In the case of an enzyme coil reactor which may have been used before the sensor, the reactor is slower because a rate can only be taken by pumping diluted sample very slowly through the reactor and monitoring the rate of reaction. Essentially no mixing takes place in the coiled tubing, and diffusion must be relied upon to bring analyte from the center of the tubing to the wall. In the present method, the analysis is faster than having a coil reactor before the sensor and faster than straight flow through.

Temperature control is easier than when carried out in a single coil reactor or gas dialyzer. Because the same segment of liquid is reciprocated back and forth in the reaction chamber during the entire analysis time, temperature control can be more concentrated and more precise. Equilibrium of the reciprocated liquid can be rapidly brought to thermal equilibrium by heating or cooling of the cuvette, reactors or the like.

Using a split coil or two reactor system of the present type allows great flexibility because miniaturizable sensors such as optical, amperometric, conductimetric, thermal or potentiometric can be utilized. In addition, multiple sensors between the coils can also be used.

While the block or housing 70 has been described as an aluminum mounting for a mixing chamber 11, reactor module and electrode, the form can bary greatly. Preferably the three components are removably mounted in the housing by spring caps or detents as is known. Supplemental heaters can be mounted in the housing to heat the components through the aluminum block. Other good heat transfer materials are also preferred for use as the housing material.

What is claimed is:

1. A method of analyzing a fluid sample to determine an analyte content thereof, said method comprising flowing said sample to a first chemical reactor and then to a second chemical reactor and reciprocating said sample between said first and second chemical reactor, and sensing the presence of said analytes conversion by said reactors into a detectable substance, said sensing carried out at a point in the flowpath of said fluid between said first and second chemical reactor.

2. A method in accordance with the method of claim 1 wherein said reactors are immobilized enzyme reactors for reacting said analyte and said analyte is reacted in said reactors.

3. A method in accordance with the method of claim 1 wherein said sensing is carried out by a sensor which has a conduit about it defining a dead space volume and each of said reactors comprises a reactor volume of at least four times said dead space volume.

4. A method in accordance with the method of claim 3 wherein each said reactor volume is at least eight times said dead space volume.

5. A method in accordance with the method of claim 4 wherein said method is carried out in a time between 0 and 5 minutes.

6. A method in accordance with the method of claim 5 wherein said analyte is glucose and said time is between 0 and 45 seconds.

7. A method in accordance with the method of claim 1 wherein said analyte is cholesterol.

8. A method in accordance with the method of claim 1 wherein said reactors comprise at least one dialyzer.

9. A method of rapidly sensing the occurrence of a chemical reaction in a fluid, said method comprising, flowing said fluid to a first chemical reactor and then to a second chemical reactor and reciprocating said fluid in a flow path between said first and second chemical reactor, while sensing at a point in said flow path between said reactors the instantaneous rate of reaction occurring in said fluid.

10. A method in accordance with claim 9 wherein said reactors are immobilized enzyme reactors.

11. A method in accordance with claim 10 wherein said sensor is an $O_2$ sensor.

12. A method in accordance with claim 11 and further comprising determining the concentration of an analyte in said fluid.

13. A method in accordance with claim 12 wherein said analyte is glucose.

14. A method in accordance with claim 12 wherein said analyte is total cholesterol.

* * * * *